US00PP15445P3

(12) United States Plant Patent
Thomsen

(10) Patent No.: US PP15,445 P3
(45) Date of Patent: Dec. 21, 2004

(54) *EUPHORBIA MILII* PLANT NAMED 'ATLAS'

(50) Latin Name: ***Euphorbia lophogona*×*E. milii***
Varietal Denomination: Atlas

(75) Inventor: Steen Thomsen, Söndersö (DK)

(73) Assignee: Gartneriet Hjortebjerg I/S (DK)

( * ) Notice: Subject to any disclaimer, the term of this patent is extended or adjusted under 35 U.S.C. 154(b) by 0 days.

(21) Appl. No.: 10/762,458

(22) Filed: Jan. 23, 2004

(65) Prior Publication Data

US 2004/0154065 P1 Aug. 5, 2004

(30) Foreign Application Priority Data

Jan. 24, 2003 (QZ) ..... PBR 20030126

(51) Int. Cl.[7] ..... A01H 5/00

(52) U.S. Cl. ..... Plt./302

(58) Field of Search ..... Plt./302

(56) References Cited

PUBLICATIONS

UPOV ROM GTITM computer database GTI Jouve Software 'Atlas'.*

* cited by examiner

*Primary Examiner*—Bruce R. Campell
*Assistant Examiner*—W C Haas
(74) *Attorney, Agent, or Firm*—Foley & Lardner, LLP

(57) ABSTRACT

A new distinct cultivar of *Euphorbia milii* plant named 'Atlas', particularly characterized by its compact plant habit; very dense and bushy plant form; moderate growth habit; abundant, large floral cymes with yellow-white bracts and red margins.

2 Drawing Sheets

Genus and species of the plant claimed: *Euphorbia lophogona*×*E. milii.*
Variety denomination: 'Atlas'.

BACKGROUND OF THE INVENTION

The present invention relates to a new and distinct cultivar of *Euphorbia* plant, botanically known as *Euphorbia lophogona*×*E. milii,* commonly known as Crown of Thorns and hereinafter referred to by the name 'Atlas'.

The new *Euphorbia* is a product of a planned breeding program conducted in Haarslev, Fyn, Denmark. The new *Euphorbia milii* originated from a cross made in 2001 by the Inventor, Steen Thomsen, with unnamed cultivars of *Euphorbia*. The male parent is an unnamed seedling of *Euphorbia milii* Desmoul. and female parent is an unnamed seedling of *Euphorbia lophogona*. The Inventor selected the new *Euphorbia* cultivar as a single plant from the progeny of the above crossing in 2001 on the basis of its flower color and compact, freely branching habit. Plants of the new *Euphorbia* are upright, compact and have a unique color and abundant medium sized flowers.

Asexual reproduction of the new cultivar by terminal cuttings taken and propagated and trial production batches at Hjortebjerg Nurseries, Denmark, has shown that the unique features of this new *Euphorbia* are stable and reproduced true to type in many successive generations of asexual reproduction.

BRIEF DESCRIPTION OF THE INVENTION

Plants of the cultivar 'Atlas' have not been observed under all possible environmental conditions. The phenotype may vary somewhat with variations in environment such as temperature, light intensity, day length, and fertility level without, however, any variance in genotype.

The following traits have been repeatedly observed and are determined to be the unique characteristics of 'Atlas'. These characteristics in combination distinguish 'Atlas' as a new and distinct cultivar:

1. Floral colors: Bracts from 158B, yellow-white to 149D yellow-green with red margins.
2. Very dense and bushy plant form.
3. Moderately vigorous, cylindrical growth habit; compact plant habit.
4. High number of flowers per plant borne on long gray-orange peduncles 177A.

Plants of the cultivar 'Atlas' can be compared to plants of the cultivar *Euphorbia milii.* 'Themis' (unpatented). Side-by-side comparisons conducted by the Inventor in Haarslev, Denmark, of the cultivar 'Atlas' and the cultivar 'Themis' have shown they differ in the following characteristics:

1. Plants of the new *Euphorbia* have striking red color and staminate cyathia with green, red bordered glands.
2. Plants of the new *Euphorbia* have smaller dark green leaves than 'Themis'.
3. Plants of the new *Euphorbia* have longer and stiffer peduncles than plants of the cultivar 'Themis'.
4. Plants of the new *Euphorbia* are more compact than the plants of the cultivar 'Themis'.
5. Plants of the new *Euphorbia* have more flowers per plant than the plants of the cultivar 'Themis'.

BRIEF DESCRIPTION OF THE PHOTOGRAPHS

The accompanying color photographic drawings illustrate the overall appearance and details of flower form, color and structures of the new cultivar, showing the colors as true as it is reasonably possible to obtain in colored reproductions of this type. Colors in the photographs may differ slightly from the color values cited in the detailed botanical description, which more accurately describe the actual colors of the new *Euphorbia*.

The first photograph shows a side perspective view of a typical flowering plant of 'Atlas' compared to 'Themis' grown in 11 cm pots.

The second photograph is a close-up of the young and older floral cymes.

DETAILED BOTANICAL DESCRIPTION

In the following description, color references are made to The Royal Horticultural Society Colour Chart, $4^{th}$ edition, where general terms of ordinary dictionary significance are used. Plants are grown under greenhouse conditions. Plants used for this description were grown for about 17 weeks after cutting and produced in 11 cm pots. Other pot sizes can be used and the plants are intended for indoor use or as a bedding plant in temperature climates while it is a perennial garden plant in tropical and subtropical areas.

Botanical classification: *Euphorbia lophogona*×*E. milii* 'Atlas'. Euphorbiaceae, Spurge family. Common English name: Crown of Thorns.

Parentage:

*Female parent.*—Unnamed seedling plant *Euphorbia lophogona.*

*Male parent.*—Unnamed seedling plant *Euphorbia milii.*

Propagation:

Type cutting: Terminal vegetative cuttings taken from plants kept in the vegetative stage by shading and high temperatures (25 C.).

Time to initiate roots: About 10 to 14 days at 18 to 21 C. in tunnels in a greenhouse.

Root description: Fine, well branched.

PLANT DESCRIPTION

Form: Perennial plant with upright, cylindrical plant habit. Flowers in cymes with cyathia subtended by colored bracts. Freely branching with about 8 lateral flowering branches forming at every node; dense and bushy. Stems are square to pentagonal with ridges about 10 mm thick at basis. By each node appears double, vertically flat, rather stiff thorns 1 large, 12 mm; 1 smaller, 5 mm. Young thorns are yellow-green: 151A; while the older ones becomes stiffer and changes color to gray (199B).

Crop time: After rooting, about 16–18 weeks are required to produce finished flowering plants in 11 cm pots.

Plant height (soil level to top of plant plane): About 18 cm. Width: 18 cm.

Vigor: Moderately vigorous growth rate.

FOLIAGE DESCRIPTION

Leaves alternate, single, obovate shape, margin entire. Length: 7 cm. Width: About 20 mm. Apex: acute. Base: cuneate to almost decussate. Texture: smooth, waxy, dull., glabrous. Color: Young foliage, upper and lower surfaces: 137B and 146C, yellow-green. Mature foliage, upper and lower surfaces: 139C and 146C respectively. Venation, 139B.

FLOWER DESCRIPTION

Flower arrangement and shape: Floral arrangements composed of cymes. The flowers (cyathia) are starkly reduced so only a ring of 5 glands and the reproductive organs are present. Subtending the cyathia are two colored bracts. The flowers are further complicated by the unique feature of funnel shaped floral buds appearing at the base of the bracts in two or more layers.

Natural flowering season: Continuous throughout the spring and summer in subtropical and tropical regions. In colder climates season can be extended by greenhouse production with high temperatures and supplementary irradiance.

Flower longevity on the plant: 5 to 9 weeks; longevity of individual flowers is highly dependent on temperature and light conditions. Bracts turn green with age. Entire cymes drop after withering.

Inflorescence size: Diameter: About 4–5 cm, height: 10 cm.

Flowers: 3 mm diameter, Bracts: overlapping at base, ovoid to inverted cordate, approximately 10 mm in length by 14 mm in width, color from 158B, yellow-white at base and center, Margins 54C, red.

Glands: 5 from N25A shiny orange to 151B yellow-green during development.

Anthers: Appear after flowers mature; stamen colors: 186C gray-purple to 165B gray-yellow, and pollen 15A, yellow-orange, Pistil and stigma: Appear before cyathia mature; color 1C, greenish-yellow.

Peduncle: Strength: strong. Length: About 7 cm. Diameter: About 2 mm. Color: 177A, gray-orange.

Pedicels: 1 cm long, 2 mm thick strong color: 177C, gray-orange.

Weather tolerance: Plants of the new *Euphorbia* have exhibited good tolerance to draught, rain and wind, however flowering may cease during cold and dark periods (<15 C.).

Pest tolerance: Plants of the new *Euphorbia* have exhibited good tolerance to following fungi: Mildew, and Thivaliopsis. Also they appear to be less infected by Thrips (Franklinellea).

I claim:

1. A new and distinct cultivar of *Euphorbia* plant named 'Atlas', as illustrated and described herein.

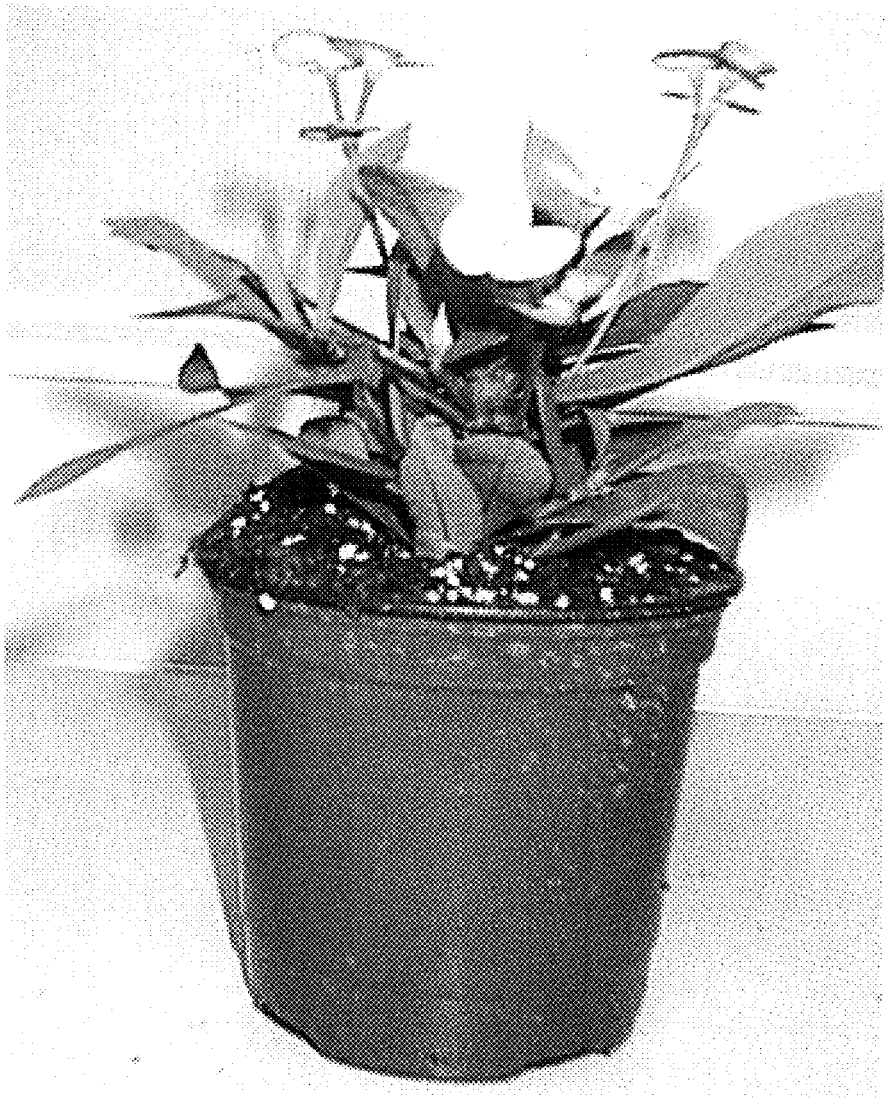

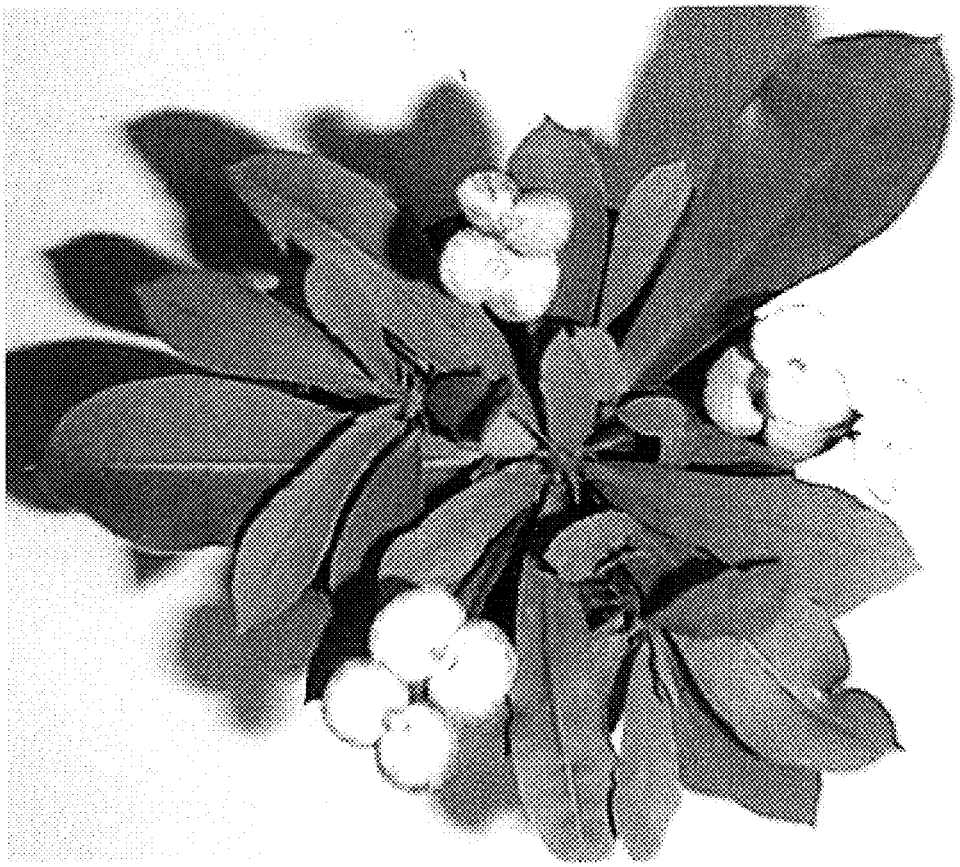

* * * * *